US010631796B2

(12) United States Patent
Oh et al.

(10) Patent No.: US 10,631,796 B2
(45) Date of Patent: Apr. 28, 2020

(54) BRAKE SYSTEM AND MEDICAL APPARATUS INCLUDING THE SAME

(71) Applicant: SAMSUNG ELECTRONICS CO., LTD., Suwon-si (KR)

(72) Inventors: Pil Yong Oh, Gwangmyeong-si (KR); Eun Hye Seo, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 161 days.

(21) Appl. No.: 15/963,328

(22) Filed: Apr. 26, 2018

(65) Prior Publication Data

US 2018/0242930 A1 Aug. 30, 2018

Related U.S. Application Data

(63) Continuation of application No. 14/862,261, filed on Sep. 23, 2015, now Pat. No. 9,974,497.

(30) Foreign Application Priority Data

Jan. 21, 2015 (KR) .................. 10-2015-0009676

(51) Int. Cl.
*H05G 1/02* (2006.01)
*A61B 6/10* (2006.01)
(Continued)

(52) U.S. Cl.
CPC .............. *A61B 6/105* (2013.01); *A61B 6/032* (2013.01); *B60T 1/14* (2013.01); *F16D 63/008* (2013.01);
(Continued)

(58) Field of Classification Search
CPC ....... A61B 6/032; A61B 6/105; A61B 6/4447; A61B 6/502; A61B 6/4405; A61B 6/4441;
(Continued)

(56) References Cited

U.S. PATENT DOCUMENTS 3,575,368 A * 4/1971 Thomas ................. A61B 6/447
248/572
4,802,198 A * 1/1989 Guenther ................. A61B 6/14
248/123.11
(Continued)

FOREIGN PATENT DOCUMENTS

CN 101200259 B 9/2010
CN 101195456 B 8/2012
(Continued)

OTHER PUBLICATIONS

Communication dated Feb. 12, 2016, issued by the Korean Intellectual Property Office in counterpart Korean Application No. 10-2015-0009676.
(Continued)

*Primary Examiner* — Irakli Kiknadze
(74) *Attorney, Agent, or Firm* — Sughrue Mion, PLLC

(57) ABSTRACT

A brake apparatus provided on a body of a medical apparatus, the brake apparatus including: a rail unit; a lever unit configured to rotate with respect to a rotational shaft; an elastic member provided on the lever unit at a first end of the lever unit and configured to provide an elastic force to rotate the lever unit; a wedge provided on a second end opposite to the first end of the lever unit, configured to be inserted into the rail unit according to rotation of the lever unit and configured to apply braking pressure on the rail unit.

12 Claims, 15 Drawing Sheets

(51) Int. Cl.
    *F16D 65/14*    (2006.01)
    *A61B 6/03*     (2006.01)
    *B60T 1/14*     (2006.01)
    *F16D 63/00*    (2006.01)
    *F16D 121/24*   (2012.01)
    *F16D 125/66*   (2012.01)
    *F16D 125/64*   (2012.01)
    *F16D 121/14*   (2012.01)
    *A61B 6/00*     (2006.01)

(52) U.S. Cl.
    CPC ............ *F16D 65/14* (2013.01); *A61B 6/4447* (2013.01); *A61B 6/502* (2013.01); *F16D 2121/14* (2013.01); *F16D 2121/24* (2013.01); *F16D 2125/64* (2013.01); *F16D 2125/66* (2013.01)

(58) Field of Classification Search
    CPC ....... A61B 6/466; A61B 6/583; A61B 6/4464; A61B 6/467; A61B 6/447; A61B 6/4476; A61B 6/548; A61B 6/547; A61B 6/4452; A61B 6/56; A61B 6/4482; A61B 6/54; A61B 6/0407; A61B 6/0457; F16D 2121/14; F16D 2121/24; F16D 2125/64; F16D 2125/66; F16D 63/008; F16D 65/14; G01N 23/04; B60T 1/14; G03B 42/025; G03B 42/026
    See application file for complete search history.

(56) References Cited

U.S. PATENT DOCUMENTS

| | | | |
|---|---|---|---|
| 5,014,828 A | 5/1991 | Baldassarre | |
| 7,543,986 B2 * | 6/2009 | Saffer | A61B 6/4441 378/196 |
| 7,734,016 B2 * | 6/2010 | Watanabe | G03B 42/02 378/117 |
| 8,020,671 B2 | 9/2011 | Kocher et al. | |
| 8,303,478 B2 * | 11/2012 | Lebosse | A61B 6/4441 600/13 |
| 8,312,972 B2 | 11/2012 | Gremaud et al. | |
| 8,480,303 B2 * | 7/2013 | Hartwich | A61B 6/4441 378/193 |
| 8,672,543 B2 * | 3/2014 | Kralles | A61B 6/4405 378/102 |
| 2001/0053203 A1 | 12/2001 | Ishii et al. | |
| 2008/0135345 A1 | 6/2008 | Kocher et al. | |
| 2010/0067652 A1 | 3/2010 | Shindo | |
| 2011/0222667 A1 | 9/2011 | Gregerson et al. | |
| 2013/0077765 A1 | 3/2013 | Welsh | |

FOREIGN PATENT DOCUMENTS

| | | |
|---|---|---|
| JP | 06-178769 A | 6/1994 |
| JP | 2002-263096 A | 9/2002 |
| KR | 10-2008-0100212 A | 11/2008 |
| KR | 10-1361473 B1 | 2/2014 |
| WO | 2014/116062 A1 | 7/2014 |

OTHER PUBLICATIONS

Communication dated Jan. 26, 2016, issued by the International Searching Authority in counterpart International Application No. PCT/KR2015/010425 (PCT/ISA/210).

Communication issued by the European Patent Office dated Jan. 10, 2018 in counterpart European Patent Application No. 15879048.5.

Communication dated Jan. 6, 2020 by the State Intellectual Property Office of P.R. China in counterpart Chinese Patent Application No. 201580073474.1.

* cited by examiner

BRAKE SYSTEM AND MEDICAL APPARATUS INCLUDING THE SAME

CROSS-REFERENCE TO RELATED APPLICATION

This application is a Continuation application Ser. No. 14/862,261 filed Sep. 23, 2015, which claims priority from Korean Patent Application No. 10-2015-0009676, filed on Jan. 21, 2015 in the Korean Intellectual Property Office, the disclosure of which is incorporated herein by reference in its entirety.

BACKGROUND

1. Field

Apparatuses consistent with exemplary embodiments relate to a brake system and a medical apparatus including the same.

2. Description of the Related Art

Radiation imaging apparatuses are imaging systems which radiate radiation, for example, X-rays onto an object such as the whole or a part of the human body or another object to obtain images from, such as an internal material, structure, or organization of a baggage.

Radiation imaging apparatuses are used as medical imaging systems for detecting an abnormality such as a lesion inside a human body, used as an image capture device to check an internal structure of an object or a component, or used as a scanning device to scan baggage at the airport.

Radiation imaging apparatuses include a computed tomography (CT) scanner. A CT scanner surrounds a moving object, continuously irradiates radiation on the moving object from all directions (i.e., around 360 degrees) and detects rays passing through the object to obtain a plurality of cross-sectional images of the object. The CT scanner continuously irradiates radiation on the object from the beginning to the end of scanning to obtain consecutive cross-sectional images thereof.

To obtain clear images of various parts of the object, a body of the CT scanner may be operated to be tilted. The body of the CT scanner may rotate at a high speed and irradiate radiation to the object while tilting at a predetermined angle. Here, when the body of the CT scanner is moving while tilting, the quality of images obtained using X-rays may be negatively impacted.

SUMMARY

One or more exemplary embodiments provide a tomograph capable of obtaining clear images of an object by preventing the movement of a body.

Additional aspects of the inventive concept will be set forth in part in the description which follows and, in part, will be obvious from the description, or may be learned by practice of the inventive concept.

In accordance with an aspect of an exemplary embodiment, there is provided a medical apparatus including a body rotatably provided to perform computed tomography (CT) scan, a base frame configured to support the body, a rail unit mounted on an outer surface of the body, and a brake system mounted on the base frame and configured to perform braking of a rotation of the body. The brake system includes a lever unit rotatably provided on a rotational shaft, and a wedge connected to one side of the lever unit and having tapered both sides. An inner surface of the rail unit is formed to be tapered to correspond to an outer surface of the wedge.

When the wedge pressurizes the inner surface of the rail unit, the body may not move.

The rotational shaft may be provided more adjacent to one side of the lever unit than the other side of the lever unit.

The lever unit may receive a driving force from a motor and rotate on the rotational shaft.

A gear part connected to a driving gear part connected to the motor may be provided on the other side of the lever unit.

The driving force of the motor may be transferred to the lever unit while being amplified by a gear ratio of the driving gear part to the gear part.

The gear part may be engaged with a connection gear part, and the connection gear part may be engaged with the driving gear part.

The brake system may further include an elastic member which supplies an elastic force to the lever unit to allow the one side of the lever unit to be separate from the rail unit.

The elastic member may be located more adjacent to the other side of the lever unit than the one side of the lever unit and may transfer the elastic force to a bottom surface of the lever unit.

A protrusion may be provided on the bottom surface of the lever unit, and the elastic member may be mounted on the protrusion.

A frictional pad may be mounted on the outer surface of the wedge.

The brake system may further include a base plate mounted on the base frame and the lever unit is rotatably mounted on the base plate.

A fixing bracket may be mounted on the base plate, and the rotational shaft may pass through the fixing bracket and the lever unit.

A hole may be formed in the base plate, and the wedge may pass through the hole and may be inserted into the rail unit.

The rail unit may include a bottom part and side parts provided on both sides of the bottom part to face each other, and a distance between the both side parts may become farther from the bottom part toward ends of the side parts.

In accordance with an aspect of another exemplary embodiment, there is provided a tomograph including a body rotatably provided to perform a CT scan, a base frame configured to support the body, a rail unit mounted on an outer surface of the body, and a brake system mounted on one of the body and the base frame and configured to prevent the movement of the body. The brake system includes a lever unit rotatably provided on a rotational shaft and a wedge connected to the lever unit and configured to be inserted into the rail unit. An outer surface of the wedge and an inner surface of the rail unit are formed to be tapered.

The brake system may further include a motor configured to transfer a driving force through the other side of the lever unit.

A gear part may be provided on the other side of the lever unit, the motor and the other side of the lever unit may be connected by a connection gear part.

The driving force of the motor may be transferred to the lever unit while being amplified by a gear ratio of the connection gear part to the gear part.

The rotational shaft may be configured more adjacent to one side of the lever unit than the other side of the lever unit.

A frictional member may be mounted on the outer surface of the wedge.

The frictional member may include rubber.

The brake system may further include an elastic member configured to supply an elastic force to allow the wedge to pressurize the inner surface of the rail unit.

In accordance with an aspect of yet another exemplary embodiment, there is provided a brake system which may perform braking of a tiltable body including a lever unit rotatably provided on a rotational shaft, a wedge which has a tapered outer surface, is provided on one side of the lever unit, and halts the movement of the body by pressurizing one side of the body, and a motor which transfers a driving force through the other side of the lever unit. The rotational shaft is located more adjacent to the one side of the lever unit than the other side of the lever unit.

The brake system may further include an elastic member which provides an elastic force to the lever unit to allow the wedge to pressurize the one side of the body.

A frictional member may be provided on the outer surface of the wedge.

A gear part may be provided on the other side of the wedge, and the driving force of the motor may be transferred to the lever unit while being amplified by a gear ratio of a connection gear part connected to the motor to the gear part.

In accordance with an aspect of yet another exemplary embodiment, there is provided a brake apparatus provided on a body of a medical apparatus, the brake apparatus including: a rail unit; a lever unit configured to rotate with respect to a rotational shaft; an elastic member provided on the lever unit at a first end of the lever unit and configured to provide an elastic force to rotate the lever unit; a wedge provided on a second end opposite to the first end of the lever unit, configured to be inserted into the rail unit according to rotation of the lever unit and configured to apply braking pressure on the rail unit.

The wedge may include an outer surface including: a first side of the wedge; and a second side of the wedge opposite to the first side of the wedge wherein the first and the second sides of the wedge are tapered.

An inner surface of the rail unit may be tapered to correspond to the outer surface of the wedge.

The wedge may be configured to apply pressure to the inner surface of the rail unit and configured to halt a movement of the body of the medical apparatus.

The brake apparatus may further include a motor configured to transfer a driving force to the lever unit.

The lever unit may include a gear part provided at the first end of the lever unit and connected to a driving gear part of the motor.

A gear ratio of the driving gear part to the gear part may be configured to amplify the driving force of the motor transferred to the lever unit.

The gear part of the lever unit may be engaged with a connection gear part, and wherein the connection gear part is engaged with the driving gear part of the motor.

The wedge may be configured to halt at least one of a linear movement and a rotation of the body of the medical apparatus.

The rotational shaft may be provided closer to the second end of the lever unit than the first end of the lever unit.

The elastic member may be configured to provide the elastic force to the lever unit and to pressurize the rail unit with the wedge.

The elastic member may be provided closer to the first end of the lever unit than the second end of the lever unit.

The wedge may include a frictional member provided on an outer surface of the wedge.

The lever unit may include a protrusion provided on a bottom surface of the lever unit, and the protrusion may be fitted in the elastic member.

The wedge may include a trapezoidal cross-sectional shape, and an inner surface of the rail unit may have a shape corresponding to the trapezoidal cross-sectional shape of the wedge.

In accordance with an aspect of yet another exemplary embodiment, there is provided a medical apparatus including: a body configured to perform a scan; a base frame configured to support the body; and a brake apparatus configured to perform braking of a movement of the body, wherein the brake apparatus includes: a rail unit attached to one of the body and the base frame; a lever unit provided on the other one of the body and the base frame and configured to rotate with respect to a rotational shaft; a motor configured to provide a driving force to the lever unit; an elastic member provided at a first end portion of the lever unit and configured to provide an elastic force; and a wedge provided on a second end portion opposite to the first end portion of the lever unit and configured to perform braking of the body.

Opposite surfaces of the wedge may be tapered, and an inner surface of the rail unit may have a shape corresponding to an outer surface including the tapered opposite surfaces of the wedge.

The elastic member may be configured to supply the elastic force to rotate the lever unit to apply braking pressure to the rail unit via the wedge.

A frictional pad may be provided on an outer surface of the wedge.

The lever unit may be rotatably provided on the rotational shaft, and the rotational shaft may be provided closer to the second end portion of the lever unit than the first end portion of the lever unit.

In accordance with an aspect of yet another exemplary embodiment, there is provided a brake apparatus provided on a body of a tomograph which performs a computed tomography (CT) scan on an object, the brake apparatus including: a lever unit rotatably provided on a rotational shaft to rotate with respect to the rotational shaft; an elastic member provided at a first end of the lever unit and configured to supply an elastic force; a wedge provided on a second end opposite to the first end of the lever unit and configured to perform braking; and a rail unit configured to perform the braking by engaging with the wedge, wherein the wedge is configured to apply braking pressure to the rail unit due to the elastic force and configured to halt tilting of the body.

The elastic member may be configured to supply the elastic force to allow the wedge to apply pressure to the rail unit.

In accordance with an aspect of yet another exemplary embodiment, there is provided a brake apparatus provided on a medical apparatus including a body performing a scan and a base frame supporting the body, the brake apparatus including: a rail unit attached to one of the body and the base frame; and a lever unit provided on the other one of the body and the base frame, the lever unit configured to engage with the rail unit, wherein the lever unit includes: a base plate attached to the other one of the body and the base frame; a bracket body provided on the base plate; a lever configured to rotate with respect to a rotational shaft inserted through the bracket body; an elastic member provided at a first end portion of the lever and configured to provide an elastic force to rotate the lever; and a wedge provided on a second end portion opposite to the first end portion of the lever unit and configured to perform braking of the body with respect to the base frame by contacting the rail unit according to rotation of the lever.

The brake apparatus may further include a motor configured to transfer a driving force to the lever unit.

The lever may include a gear part provided at the first end of the lever and connected to a driving gear part of the motor.

BRIEF DESCRIPTION OF THE DRAWINGS

The above and/or other aspects of the disclosure will become apparent and more readily appreciated from the following description of the embodiments, taken in conjunction with the accompanying drawings of which.

DETAILED DESCRIPTION

Hereinafter, exemplary embodiments will be described in detail with reference to the attached drawings.

Figure 1:
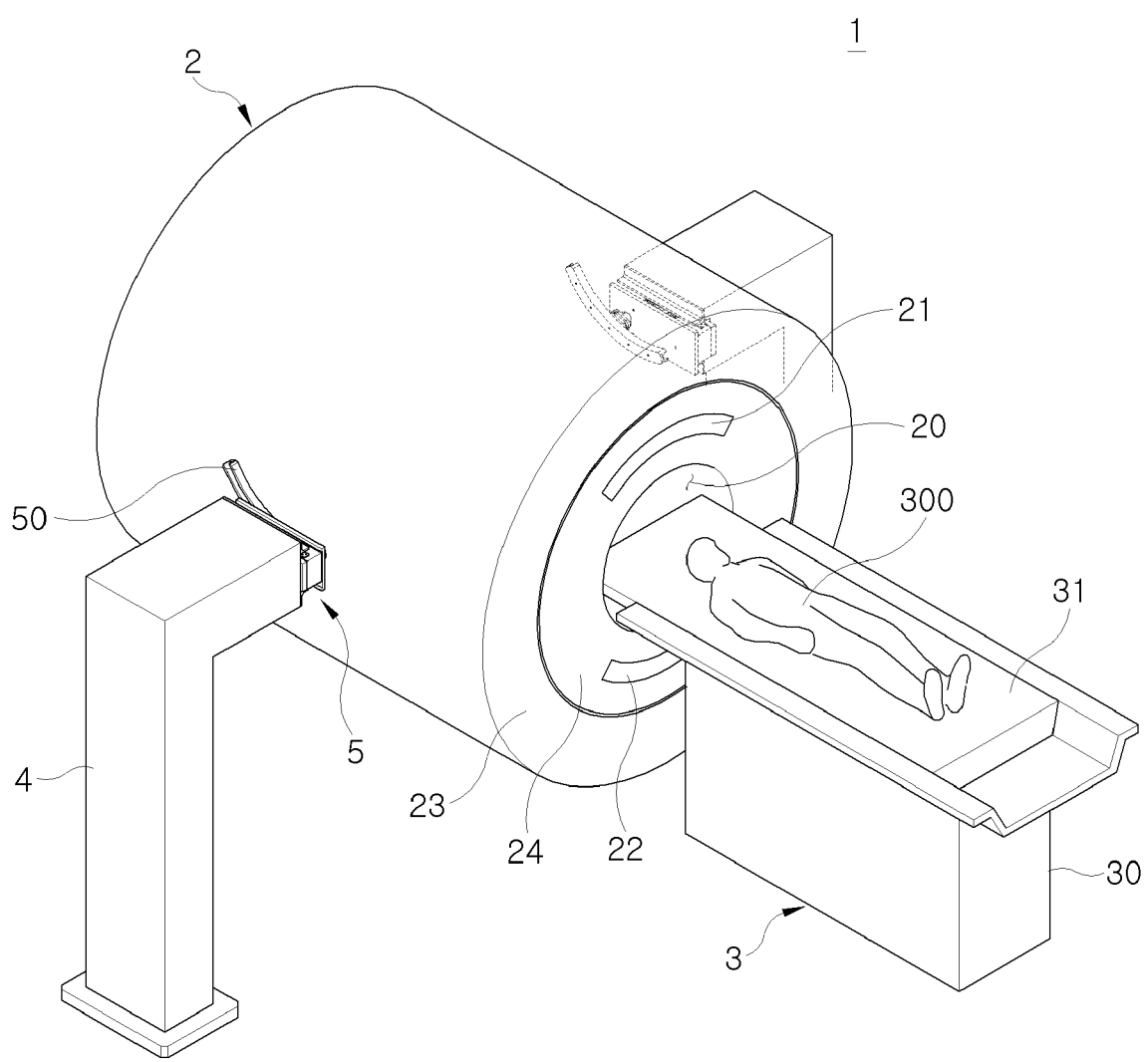
FIG. 1 is a perspective view of a medical apparatus according to an exemplary embodiment.
Figure 2:
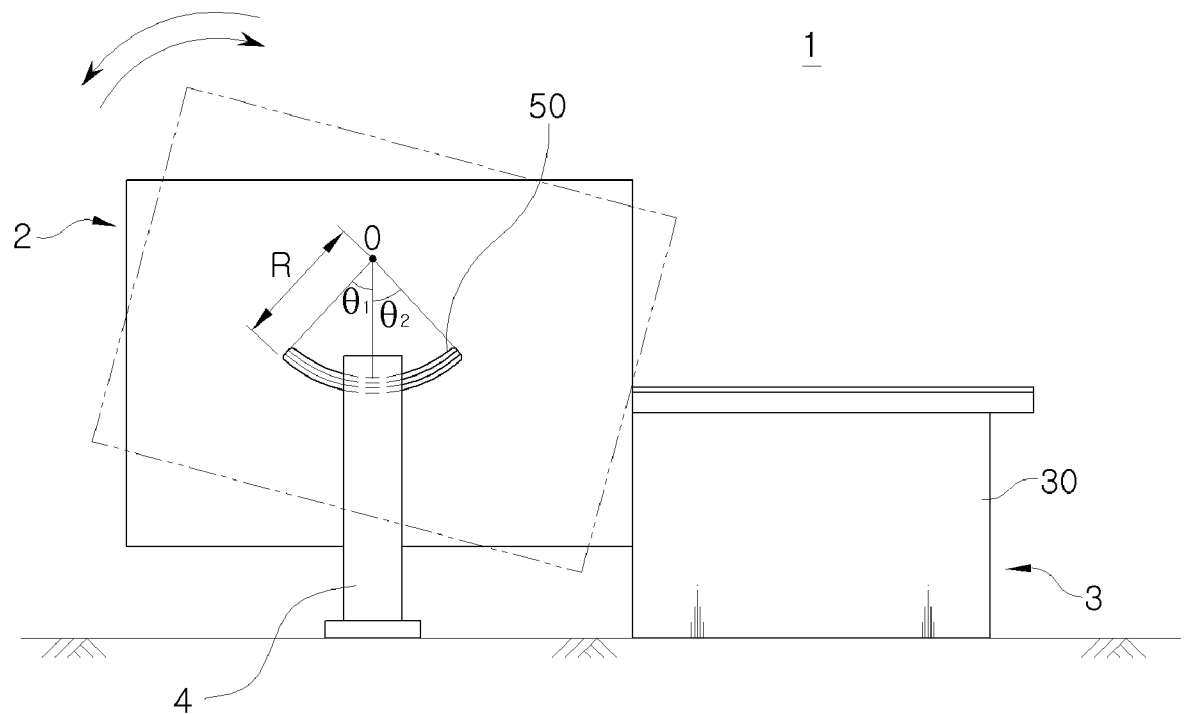
FIG. 2 is a side view of a body according to an exemplary embodiment.

FIG. 1 is a perspective view of a medical apparatus 1 according to an exemplary embodiment. FIG. 2 is a side view of a body 2 according to an exemplary embodiment.

Referring to FIGS. 1 and 2, the medical apparatus 1 includes the body 2 and an examination stand 3. The body 2 may include an opening 20 in a center part and an X-ray generator 21 and an X-ray detector 22 disposed thereinside to be opposite to each other. An object 300 located on the examination stand 3 may be inserted into the opening 20 to perform tomography scanning.

The body 2 includes a stator 23 and a rotor 24 in which the opening 20 is installed in the center thereof. The rotor 24 may be rotatably provided inside the stator 23. The X-ray generator 21 may be provided on one side of the rotor 24, and the X-ray detector 22 may be provided on the other side of the rotor 24. The X-ray generator 21 and the X-ray detector 22 may be provided to be opposite to each other.

When a current is supplied to the stator 23, the rotor 24 rotates thereinside, X-rays generated by the X-ray generator 21 are radiated onto the object 300, and X-rays passing through the object 300 may be detected by the X-ray detector 22.

The X-ray detector 22 may directly receive X-rays which pass through the object 300 or X-rays which are radiated to the periphery of the object 300 and do not reach the object 300, and may detect the X-rays by conversion into electric signals. The medical apparatus 1 may further include an image processor which reads and generates images from the electric signals stored in the X-ray detector 22, image-processes the generated images, or generates other images using the generated images. Also, the medical apparatus 1 may further include a controller for controlling whether X-rays are radiated or not.

The body 2 may be supported by a base frame 4. The base frame 4 may be provided on both left and right sides of the body 2. The base frame 4 may be mounted outside the stator 23. To obtain definite images of the object 300, the body 2 may be mounted on the base frame 4 to be tiltable. As shown in FIG. 2, the body 2 may be provided to be tiltable to allow a front side thereof to move up and down.

A brake system (or a brake apparatus) 5 may be provided between the body 2 and the base frame 4. One of an outer surface of the body 2 and the base frame 4 may include a rail unit 50 and the other may include the brake system 5. In the exemplary embodiment, the rail unit 50 may be provided on the outer surface of the body 2 and the brake system 5 may be provided on one side of the base frame 4. A portion of the brake system 5 may be provided to be insertable into the rail unit 50.

As shown in FIG. 2, the rail unit 50 is provided to have a predetermined curvature in such a way that the rail unit 50 moves together with the body 2 and the portion of the brake system 5 inserted into the rail unit 50 may vary in position along the rail unit 50 when the body 2 tilts. The rail unit 50 may be provided to have a proper curvature and length depending on a tilt angle and shape of the body 2.

The rail unit 50 may be a part of a circle having a radius R and having a rotational center O as shown in FIG. 2. When the radius R increases, the occurrence of vibrations of the body may be reduced and the braking property of the brake system 5 may be improved. However, when the radius R of the body 2 increases, a range of tilt angles ($\theta1+\theta2$) may be reduced. To obtain definite images of the object 300, the body 2 may be provided to operate at an tilt angle of about 60°. For example, based on when the body 2 does not tilt, that is, a front and rear of the body 2 are located in parallel to a bottom surface, a tilt angle $\theta1$ to allow the front of the body 2 to face downward and a tilt angle $\theta2$ to allow the front of the body 2 to face upward may be provided to be about 30°, respectively. Here, the radius R may be present within a range of 400 mm to 440 mm. More specifically, the radius R may be about 420 mm.

Due to the brake system 5, the body 2 may be fixed not to move while tilting even when the rotor 24 rotates. A detailed configuration of the brake system 5 will be described below.

The examination stand 3 includes a supporter 30 and a transfer unit 31. The transfer unit 31 may be slidably provided above the supporter 30. When the object 300 is located on the transfer unit 31, the transfer unit 31 slides to be inserted into the body 2 through the opening 20. When the object 300 is inserted into the opening 20, the object 300 may be located between the X-ray generator 21 and the X-ray detector 22. The rotor 24 rotates on the object 300, and images of the object 300 from various angles may be taken using X-rays generated by the X-ray generator 21.

Hereinafter, an exemplary embodiment in which the rail unit 50 is provided on the outer surface of the body 2 and the brake system 5 is provided on one side of the base frame 4 will be described.

Figure 3A:
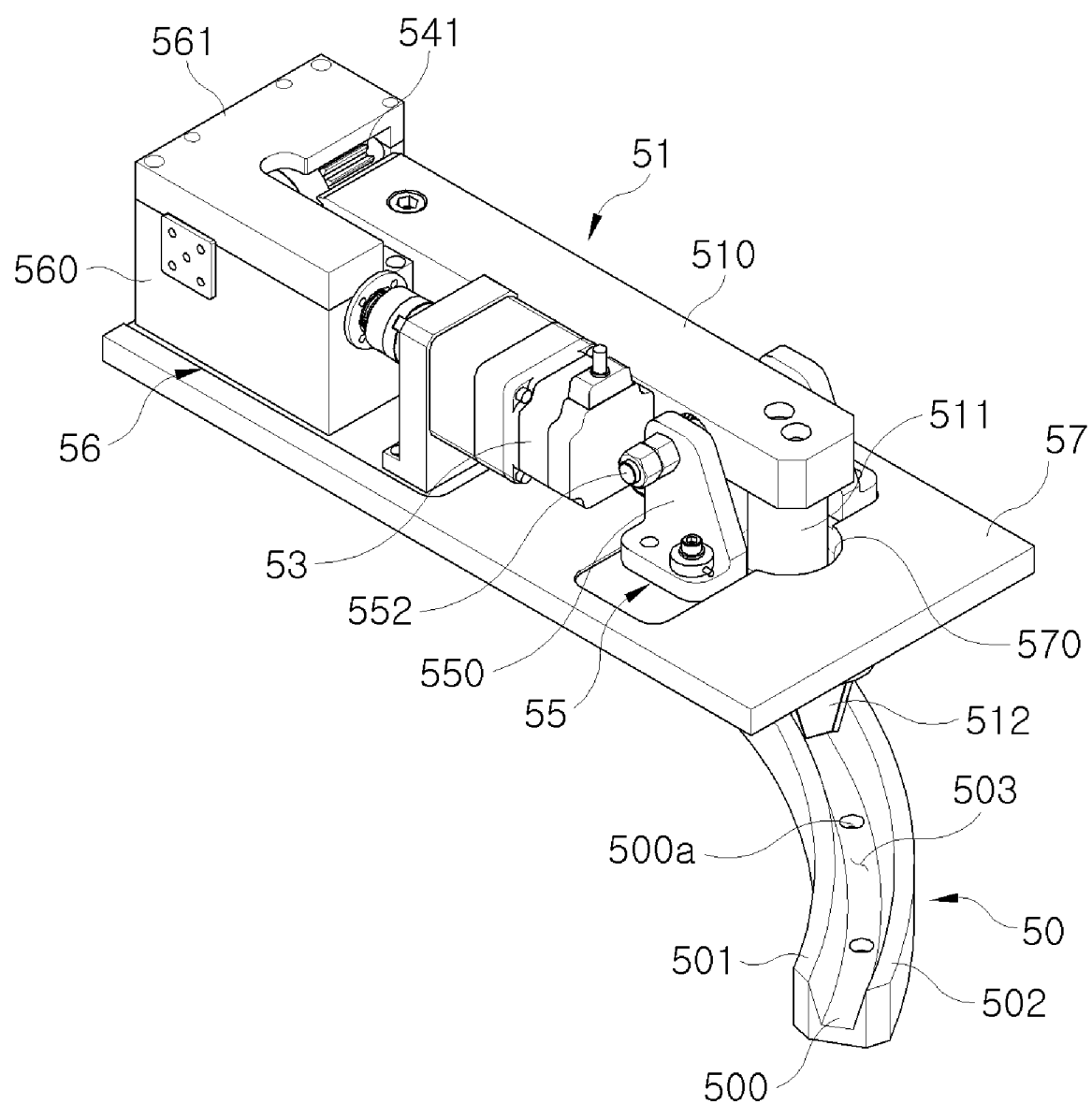
FIGS. 3A and 3B are perspective views of a brake system according to an exemplary embodiment.
Figure 3B:
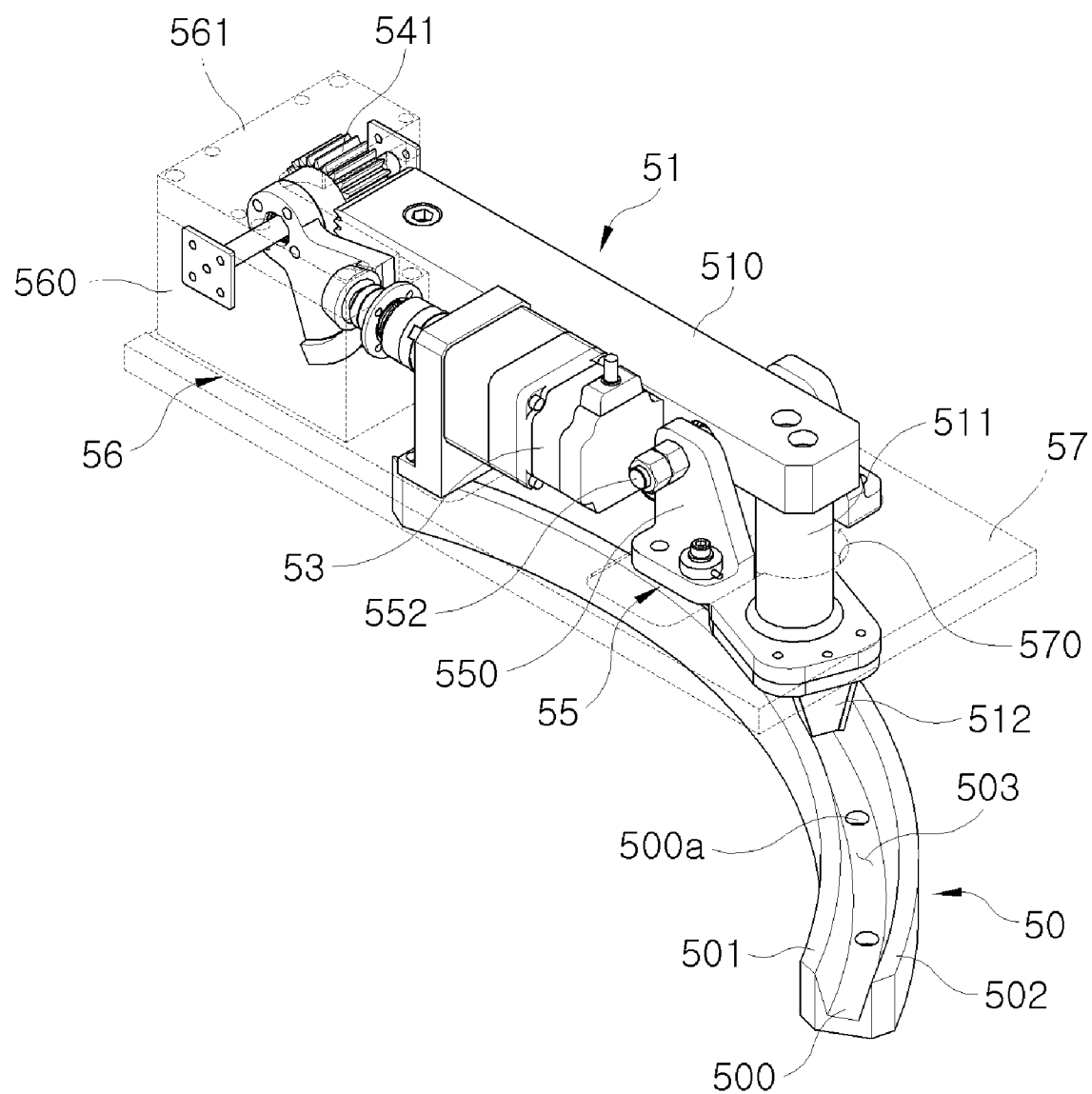
Figure 4:
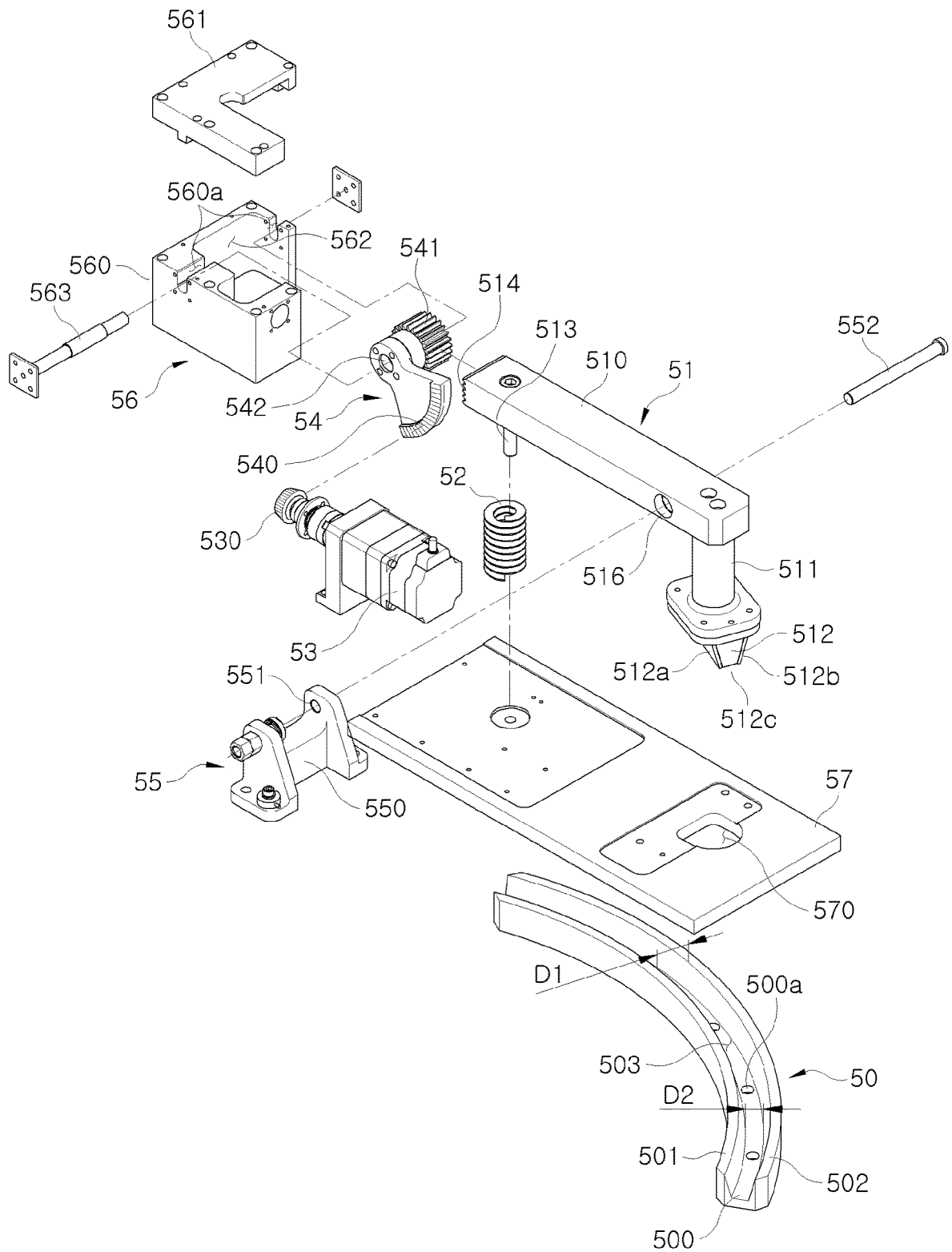
FIG. 4 is an exploded perspective view of the brake system according to an exemplary embodiment.

FIGS. 3A and 3B are perspective views of the brake system 5 according to an exemplary embodiment. FIG. 4 is an exploded perspective view of the brake system 5.

Referring to FIGS. 3A, 3B and 4, the brake system 5 is provided on one surface (i.e., a surface facing the body 2) of the base frame 4 to allow a part of a lever unit 51 to be insertable into the rail unit 50 provided on the outer surface of the body 2. As the body 2 tilts, a position of the lever unit 51 with respect to the rail unit 50 may vary.

The rail unit 50 may include a bottom part 500 and side parts 501 and 502 extending or protruding from the bottom part 500. The side parts 501 and 502 may be provided on both sides of the bottom part 500 to be opposite to each other. A sliding part 503 in which the lever unit 51 is inserted and moves may be formed by the bottom part 500 and the side parts 501 and 502. The bottom part 500 may include a plurality of coupling holes 500a. The rail unit 50 may be mounted on the outer surface of the body 2 by a coupling member passing through the plurality of coupling holes 500a.

Inner surfaces of the side parts 501 and 502 may be provided to be tapered. Specifically, a greater distance between the inner surfaces of the side parts 501 and 502 may be formed farther away from the bottom part 500. That is, a distance D1 between ends of the side parts 501 and 502 located farthest from the bottom part 500 may be formed to be greater than a distance D2 between parts of the side parts 501 and 502 adjacent to the bottom part 500.

The brake system 5 may include the lever unit 51, an elastic member 52 which provides the lever unit 51 with an elastic force, and a driving source 53 capable of driving the lever unit 51. The lever unit 51, the elastic member 52, and the driving source 53 may be provided on a base plate 57. The base plate 57 may be mounted on the surface of the base frame 4 facing the body 2.

The lever unit 51 includes a first lever part 510 and a second lever part 511. The second lever part 511 may be provided to extend or protrude from one side (i.e., a bottom side facing the rail unit 50) of the first lever part 510 to form an approximate right angle. The second lever part 511 may be provided adjacent to the one end (i.e. a first end/a first side) of the first lever part 510. A wedge 512 may be provided on an end of the second lever part 511. A hole 570 may be formed in one side of the base plate 57. The wedge 512 may pass through the hole 570 and may be inserted into the sliding part 503 of the rail unit 50.

The wedge 512 may be provided to correspond to a shape of an inner surface of the rail unit 50 which forms the sliding part 503. Outer surfaces 512a and 512b of the wedge 512 may be formed to correspond to tapered shapes of the inner surfaces of the side parts 501 and 502 of the rail unit 50. That is, a distance between the outer surfaces 512a and 512b which face each other may be provided to become smaller toward an end of the wedge 512 (i.e., an end provided closer to the rail unit 50). Due to a rotation of the first lever part 510, a bottom surface 512c of the wedge 512 may be in contact with the bottom part 500 of the rail unit 50 according to a rotational position of the first lever part 510.

The elastic member 52 may be mounted on one side (i.e., a bottom side) of the first lever part 510.

A protrusion 513 may be further provided on the one side of the first lever part 510, and the elastic member 52 may be mounted on the protrusion 513. That is, the elastic member 52 is engaged with the first lever part 510 by the protrusion 513 being inserted in the elastic member according to the exemplary embodiment. The protrusion 513 may be provided adjacent to the other end (i.e., a second side/a second end) of the first lever part 510.

In detail, the elastic member 52 may fit on the protrusion 513 and may be located between one surface of the first lever part 510 and one surface of the base plate 57, thereby providing a bottom surface of the first lever part 510 with an elastic force. The elastic member 52 may apply the elastic force to allow the bottom surface at the other end (i.e. the second end) of the first lever part 510 to become farther from the base plate 57. When the bottom surface at the other end (i.e., the second end) of the first lever part 510 becomes farther from the base plate 57, in turn, the wedge 512 may be pushed toward the rail unit 50 and apply braking pressure to the body 2.

In the above described exemplary embodiment, the elastic member 52 is provided adjacent to the other end (i.e., the second end opposite to the first end where the wedge 512 is located) of the first lever part 510 and provides the bottom surface of the first lever part 510 with the elastic force. However, an installation position and a pressurization position of the elastic member 52 are not limited thereto. For example, the elastic member 52 may be provided adjacent to the one end (i.e., the first end where the wedge 512 is located) of the first lever part 510 and may apply the elastic force a top surface of the first end of the first lever part 510 to perform braking. Hereinafter, a case in which the elastic member 52 is provided on the other end of the first lever part 510 (i.e., the second end opposite to the first end where the wedge 512 is located) and applies the elastic force to the bottom surface of the first lever part 510 will be described.

A gear part 514 may be provided on the other end (i.e., the second end) of the first lever part 510 in the exemplary embodiment. The gear part 514 may be engaged with a gear part 541 connected to a motor 53 that will be described below. A gear ratio of the gear part 514 provided on the other end of the first lever part 510 to the gear part 541 connected to the motor 53 is suitably adjusted to amplify and transfer a driving force from the motor 53 to the first lever part 510.

A rotational shaft 552 may be provided between the second lever part 511 and the protrusion 513. A through hole 516 may be formed in the first lever part 510, and the rotational shaft 552 may be provided to pass through the through hole 516. The through hole 516 may be formed to pass through between the second lever part 511 and the protrusion 513. Accordingly, the rotational shaft 552 may be provided to extend in a widthwise direction of the first lever part 510.

The rotational shaft 552 may be provided closer to the one end of the first lever part 510 provided with the second lever part 511 than the other end of the first lever part 510. In the exemplary embodiment, due to a leverage effect, the driving force applied on the other end of the first lever part 510 may be transferred to the one end of the first lever part 510 while being amplified. When the driving force of the motor 53 is transferred to the other end of the first lever part 510, the force transferred to the other end of the first lever part 510 is transferred to the one end of the first lever part 510 while being amplified. Accordingly, the wedge 512 applies pressure to the inner surface of the rail unit 50 using the amplified force, thereby improving the braking performance of the brake system 5 with respect to the body 2.

The base plate 57 may be provided with a fixing bracket 55 including a hole 551 into which the rotational shaft 552 is insertable. The fixing bracket 55 may be coupled with the base plate 57 using a coupling member. A bracket body 550 of the fixing bracket 55 may be provided to protrude from the one surface of the base plate 57, and the hole 551 into which the rotational shaft 552 is insertable may be formed in the bracket body 550. The rotational shaft 552 is inserted into the hole 514 formed in the first lever part 510 and the hole 551 formed in the fixing bracket 55, thereby fastening the lever unit 51 to the base plate 57 to be rotatable on the rotational shaft 552.

The motor 53 may be provided on the one side of the base plate 57. The driving force of the motor 53 may be transferred to the lever unit 51 through a link between the gear part 514 and the gear part 541. The lever unit 51 receives the driving force of the motor 53 and moves to allow the other end of the first lever part 510 to approach the base plate 57. When the other end of the first lever part 510 approaches the base plate 57, the one end of the first lever part 510 becomes farther from the base plate 57 and the wedge 512 provided on the end of the second lever part 511 located on the one end of the first lever part 510 may become separate from the inner surface of the rail unit 50.

As an example, when the motor 53 and the lever unit 51 are provided to extend in parallel due to spatial constraints of the brake system 5, the driving force of the motor 53 may be transferred to the lever unit 51 through a driving gear part 530 provided on the motor 53 and a connection gear unit 54.

The base plate 57 may be provided with a mounting bracket 56 to mount the connection gear unit 54 thereon to be rotatable. The mounting bracket 56 may include a bracket body 560 provided with a space 562, in which the connection gear unit 54 is accommodated to prevent a rotation of the connection gear unit 54 from being interfered with other parts, and a bracket cover 561 which covers an opening formed in one side of the mounting bracket 56.

The mounting bracket 56 may include a shaft insertion hole 560a into which a rotational shaft 563 is insertable. The shaft insertion hole 560a may be formed in the bracket body 560. The rotational shaft 563 may pass through the shaft insertion hole 560a and an insertion hole 542 formed in the connection gear unit 54, thereby mounting the connection gear unit 54 on the mounting bracket 56 to be rotatable.

A first connection gear part 540 engaged with the driving gear part 530 is formed on one side of the connection gear unit 54, and a second connection gear part 541 engaged with the gear part 514 formed on the other end of the first lever part 510 may be formed on the other side of the connection gear unit 54. When the motor 53 and the lever unit 51 are located in parallel, the connection gear unit 54 is formed to be bent in such a way that the first connection gear part 540 is formed on one end and the second connection gear part 541 is formed on the other end. Here, extending directions of the teeth of the gear part 514 and the second connection gear part 541 may intersect with each other.

Figure 5:
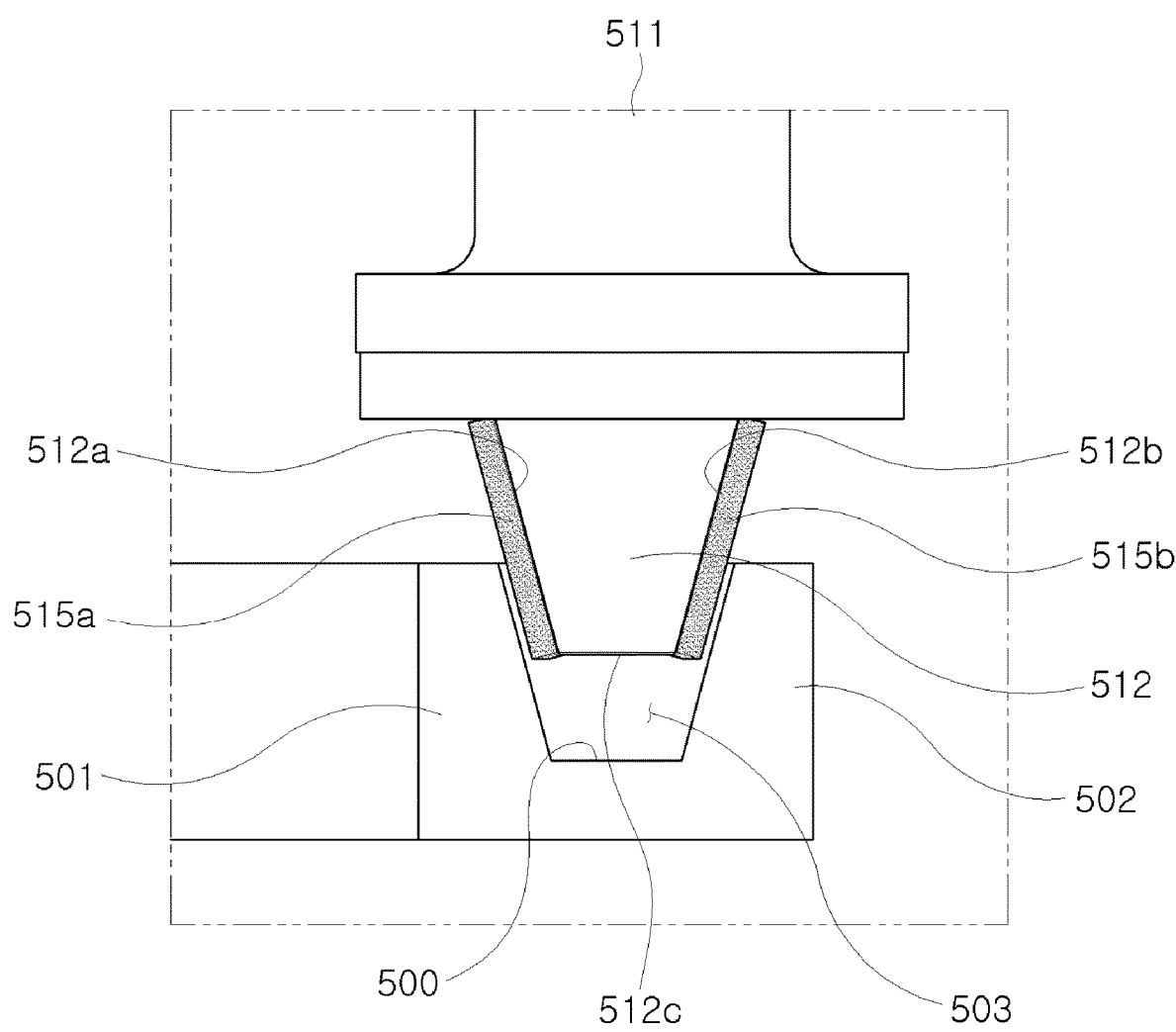
FIG. 5 is a cross-sectional view illustrating a wedge and a rail unit according to an exemplary embodiment.

FIG. 5 is a cross-sectional view illustrating the wedge 512 and the rail unit 50 according to an exemplary embodiment.

Referring to FIG. 5, frictional members (e.g., frictional pads) 515a and 515b formed of a material having a high friction coefficient may be provided on the outer surfaces 512a and 512b of the wedge 512. The frictional members 515a and 515b may be mounted on the outer surfaces 512a and 512b of the wedge 512 and may increase a frictional force between the wedge 512 and the inner surface of the rail unit 50. For example, the frictional members 515a and 515b may include a material having a high frictional force such as rubber and silicone.

The frictional members 515a and 515b are provided on the outer surfaces 512a and 512b of the wedge 512 to increase the frictional force between the wedge 512 and the rail unit 50, thereby improving the braking performance of the brake system 5.

In the above described exemplary embodiment, the frictional members 515a and 515b are provided on the outer surfaces 512a and 512b of the wedge 512. However, the exemplary embodiment is not limited thereto. For example, the frictional members may be provided on the bottom surface 512c of the wedge 512. Also, frictional members may be provided on the inner surface of the rail unit 50.

Figure 6:
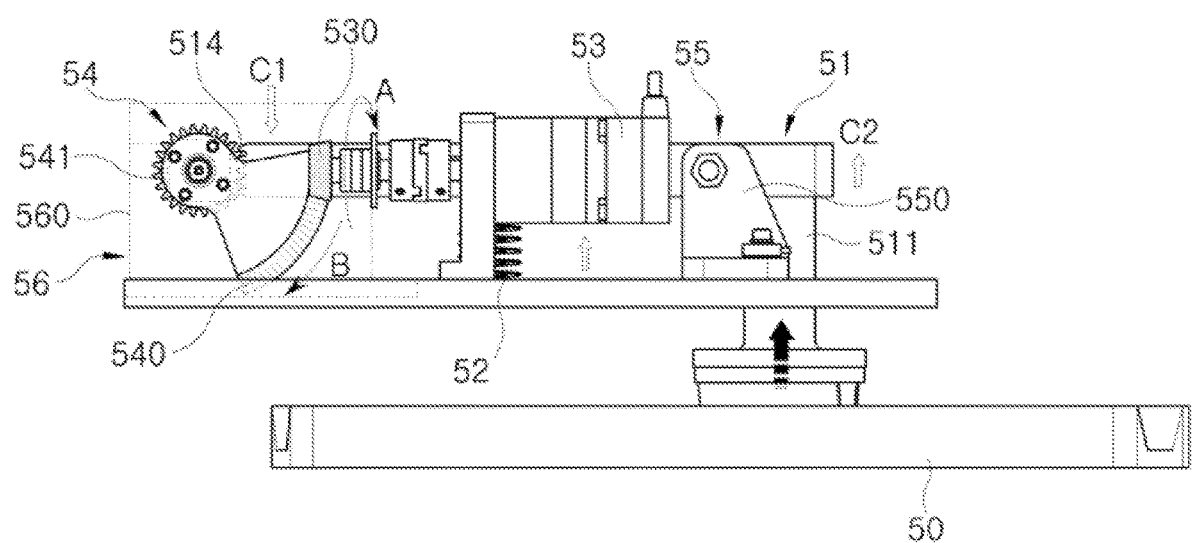
FIGS. 6 and 7 are side views of the brake system according to an exemplary embodiment.
Figure 7:
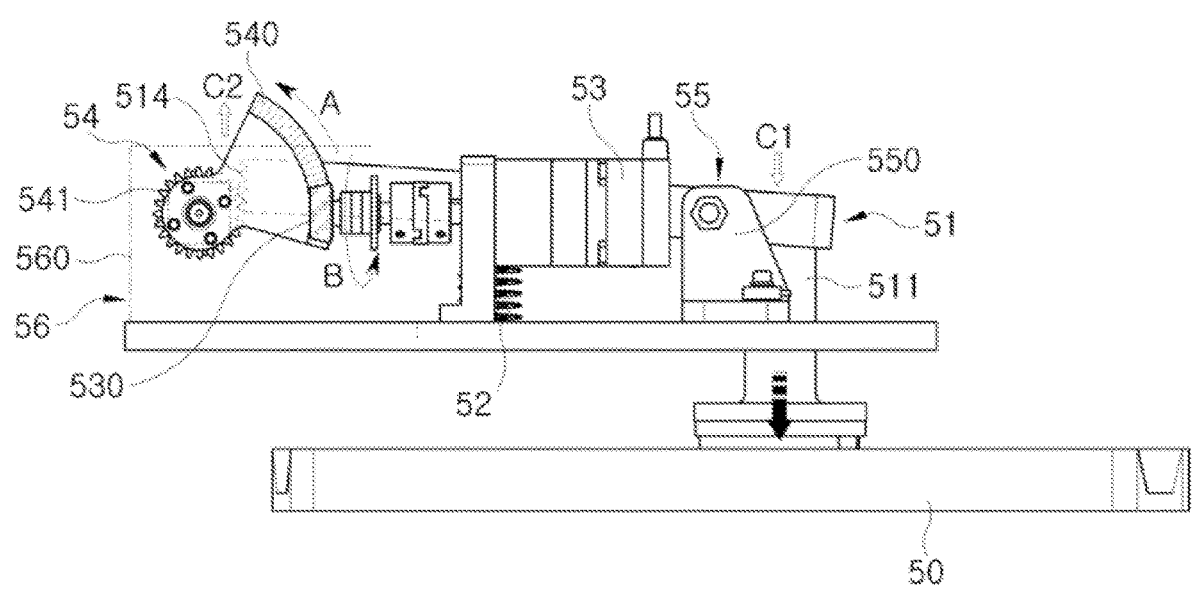

FIGS. 6 and 7 are side views of the brake system 5 according to an exemplary embodiment.

As shown in FIG. 6, when the driving gear part 530 rotates in a direction A due to the motor 53, the first connection gear part 540 may rotate in another direction B. When the first connection gear part 540 rotates in the other direction B, the gear part 514 engaged with the second connection gear part 541 may rotate in a downward direction C1 and the first lever part 510 may rotate with respect to the rotational shaft 552 such that the one end of the first lever part 510 moves closer to the base plate 57. Here, the second lever part 511 may move in an upward direction C2, and the wedge 512 connected to the second lever part 511 may become separate from the inner surface of the rail unit 50. Because the rail unit 50 is not interfered with the wedge 512, the body 2 mounted with the rail unit 50 may tilt to allow the front thereof to move up and down.

On the other hand, as shown in FIG. 7, when the driving gear part 530 rotates in the direction B due to the motor 53, the first connection gear part 540 may rotate in the direction A. When the first connection gear part 540 rotates in the direction A, the gear part 514 engaged with the second connection gear part 541 may rotate in the upward direction C2 and the first lever part 510 may rotate on the rotational shaft 552 to become farther from the base plate 57. Here, the second lever part 511 may move in the downward direction C1, and the wedge 512 connected to the second lever part 511 may be in contact with the inner surface of the rail unit 50.

When the bottom side of the first lever part 510 is pressurized by the driving force transferred from the motor 53 at one end, the wedge 512 may apply pressure the inner surface of the rail unit 50 to perform braking. The frictional force between the outer surfaces 512a and 512b of the wedge 512 and the inner surface of the rail unit 50 and the force of the wedge 512 applied to the inner surface of the rail unit 50 may fix the rail unit 50 not to move. Because the rail unit 50 is fixed by the wedge 512, the body 2 may be fixed not to tilt. As described above, because the body 2 is fixed not to move by the brake system 5, even when the rotor 24 rotates to perform radiography, the body 2 does not move, thereby obtaining definite images of the object 300.

Figure 8:
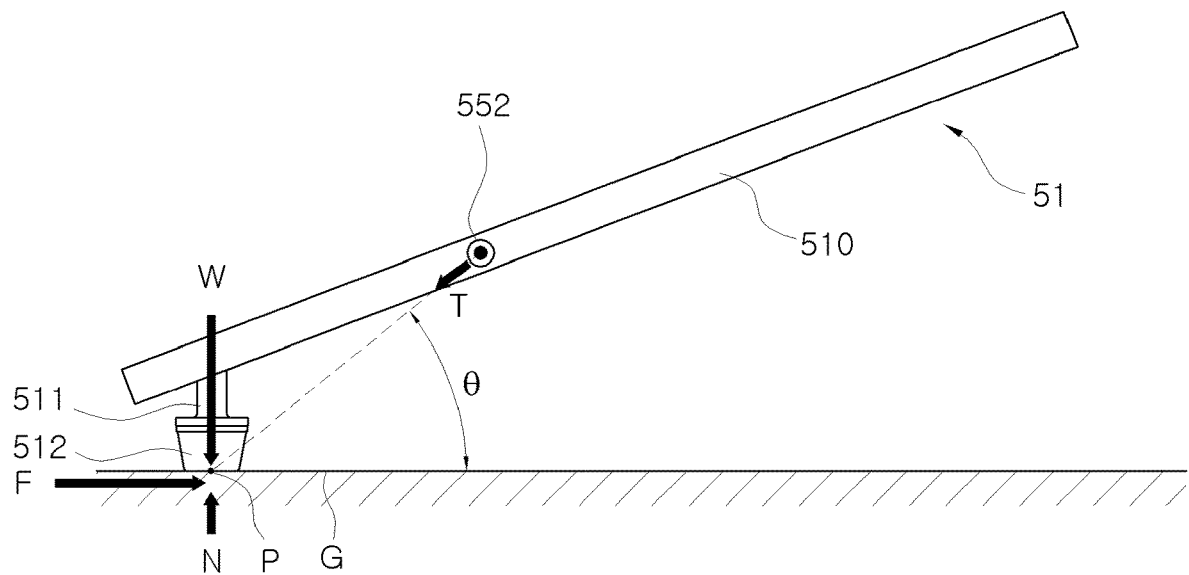
FIG. 8 is a schematic view of the brake system according to an exemplary embodiment.
Figure 9:
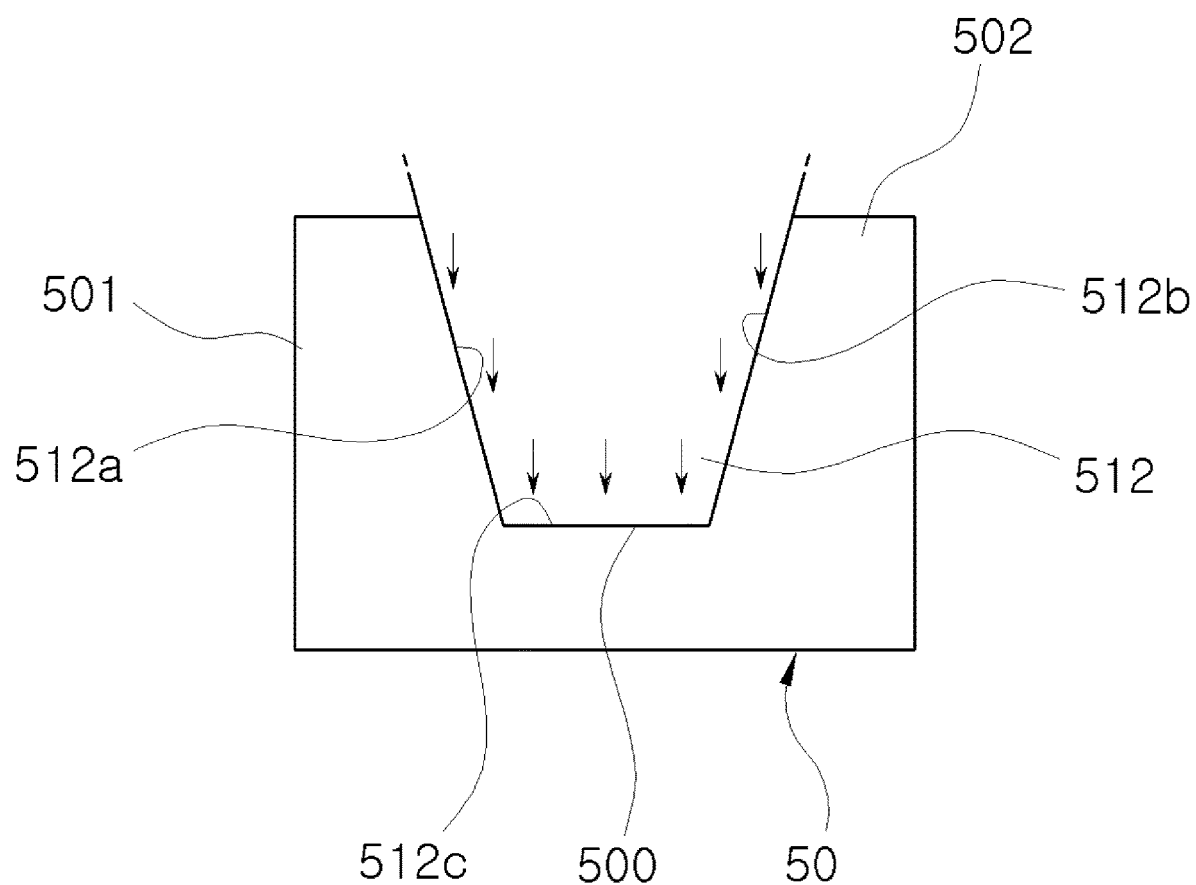
FIG. 9 is a schematic view illustrating parts of the wedge part and the rail unit according to an exemplary embodiment.

FIG. 8 is a schematic view of the brake system 5 according to an exemplary embodiment. FIG. 9 is a schematic view illustrating parts of the wedge 512 and the rail unit 50 according to an exemplary embodiment.

Referring to FIGS. 8 and 9, the lever unit 51 of the brake system 5 applies pressure to the rail unit 50 via the wedge 512, thereby fixing the rail unit 59 not to move. In the exemplary embodiment, to allow the wedge 512 to apply braking pressure to the inner surface of the rail unit 50, the first lever part 510 may receive the driving force of the motor 53 and may rotate with respect to the rotational shaft 552.

The first lever part 510 may receive the elastic force of the elastic member 52 and may rotate with respect to the rotational shaft 552. Even when the driving force of the motor 53 is not transferred to the first lever part 510, the elastic member 52 is located on the bottom surface of the first lever part 510 in such a way that the wedge 512 mounted on the second lever part 511 may apply pressure to the inner surface of the rail unit 50.

As described above, the first lever part 510 rotates with respect to the rotational shaft 552 due to one of the driving force of the motor 53 and the elastic force of the elastic member 52, thereby allowing the wedge 512 to apply pressure to the inner surface of the rail unit 50.

Hereinafter, a fixing configuration in which the body 2 does not move due to the elastic force of the elastic member 52 and the shape of the wedge 512 when the driving force of the motor 53 is not transferred to the lever unit 51 is described.

Due to the elastic force transferred from the elastic member 52, the bottom surface 512*c* of the wedge 512 may apply pressure to the bottom part 500 of the rail unit 50. As shown in FIG. 9, due to the shapes of the outer surfaces 512*a* and 512*b* of the wedge 512 and the inner surface of the rail unit 50, the outer surfaces 512*a* and 512*b* of the wedge 512 may apply braking pressure to the inner surface of the rail unit 50. In the exemplary embodiment, the wedge 512 may apply pressure to the rail unit 50 with a greater force than a case in which the outer surfaces 512*a* and 512*b* of the wedge 512 are provided to be vertical to the bottom surface 512*c* of the wedge 512 or the inner surface of the rail unit 50 is provided to be vertical to the bottom part 500 of the rail unit 50.

As shown in FIG. 8 illustrating the first lever part 510 from the side, a force applied by the wedge 512 in a vertical direction to the bottom part 500 of the rail unit 50 at one point P of the rail unit 50 may be referred to as W. A normal force at the point P may be designated as N, and a frictional force at the point P may be designated as f. Such frictional force may be expressed as f=μN, in which μ indicates a friction coefficient.

When a reaction force applied in a linear direction from rotational shaft 552 to the point P in which the first lever part 510 is fixed is designated as T, one side of the rail unit 50 on which the point P is located is designated as G, and an angle formed by T and G is designated as θ, a force applied to the point P may be expressed below.

$$\mu N - T \cos \theta = 0$$

$$-W + N - T \sin \theta = 0$$

Arranging these with respect to W, W=(T/μ)cos θ−Tsin θ.

Here, when W is smaller than 0, it is possible to fix the rail unit 50 by pressurizing the point P.

Eliminating T from the expression for W, (T/μ)cos θ−Tsin θ<0 may be arranged below.

$$(1/\mu)\cos \theta - \sin \theta < 0$$

Transposing cos θ and sin θ to the right side, it is below.

$$(1/\mu) < (\sin \theta / \cos \theta)$$

Because sin θ/cos θ is tan θ, when tan θ>1/μ the wedge 512 may pressurize the rail unit 50 to fix the body 2 not to tilt.

For example, when a friction coefficient μ is 0.4, the wedge 512 may apply pressure to the rail unit 50 to be fixed and not allow the body 2 to move when θ is greater than 70°. As described above, even when the driving force of the motor 53 is not transferred, the movement of the body 2 may be prevented while taking images due to the fixing configuration which allows the wedge 512 to apply braking pressure to the rail unit 50 due to the elastic force of the elastic member 52.

The tapered shapes of the inner surface of the rail unit 50 and the outer surfaces 512*a* and 512*b* of the wedge 512 in the brake system 5 allow the force of the wedge 512 applied to the inner surface of the rail unit 50 to be increased. Also, an output of the motor 53 may be transferred to the lever unit 51 while being amplified using the leverage effect and the gear ratio between the gears located between the motor 53 and the lever unit 51, thereby improving the performance of the brake system 5.

The frictional members 515*a* and 515*b* are attached to the outer surfaces 512*a* and 512*b* of the wedge 512, thereby increasing the frictional force with the inner surface of the rail unit 50 and preventing the degradation of the performance of the brake system 5, which occurs due to a decrease in the frictional force between the wedge 512 and the inner surface of the rail unit 50, which is caused by fluids such as water and oil therebetween. The one side of the lever unit 51 receives the elastic force from the elastic member 52, thereby fixing the wedge 512 so as not to be pushed from the inner surface of the rail unit 50 although the motor 53 is not driven.

Due to the configuration of the brake system 5 as described above, the body 2 does not move although rotating at a high speed, thereby obtaining definite images of the object 300 and improving the quality of the medical apparatus 1.

Hereinafter, another exemplary embodiment in which a brake system 6 having the structural characteristics described above is applied to another apparatus will be described.

Figure 10:
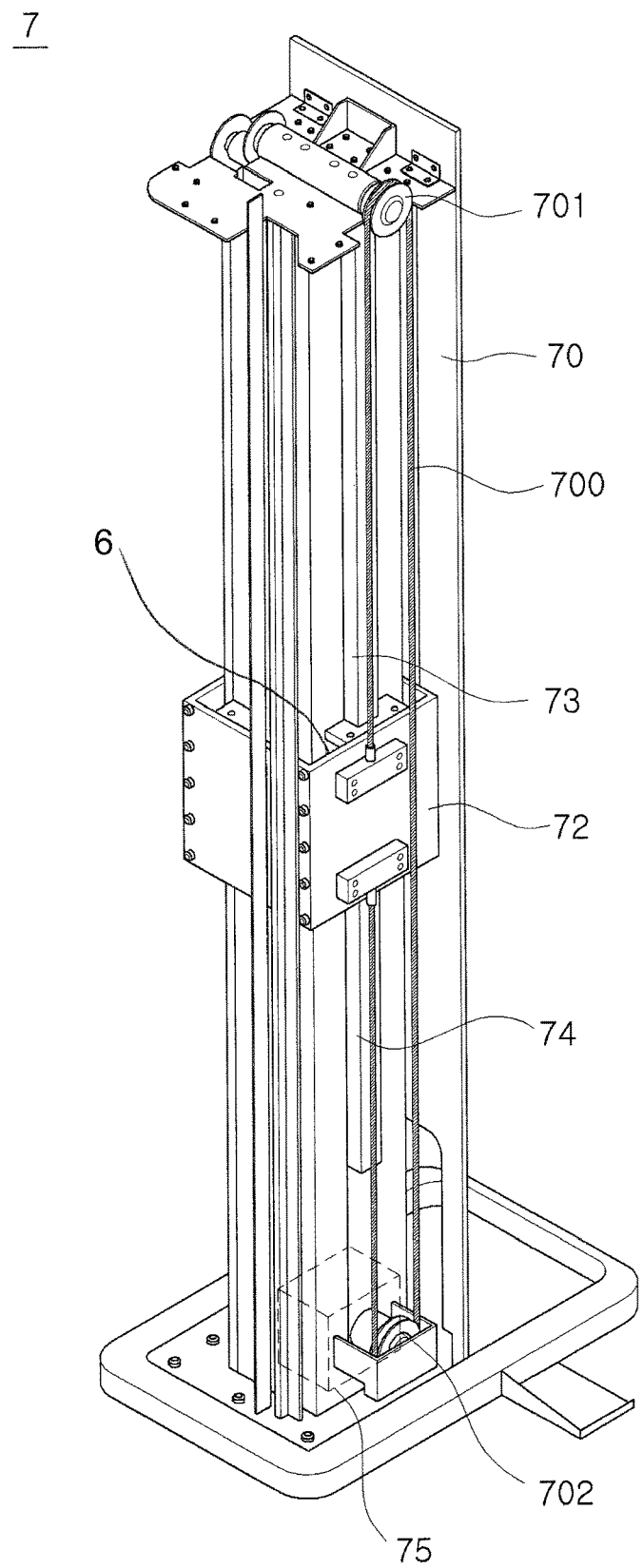
FIG. 10 is a view of a mammographic apparatus including a brake system according to an exemplary embodiment.
Figure 11:
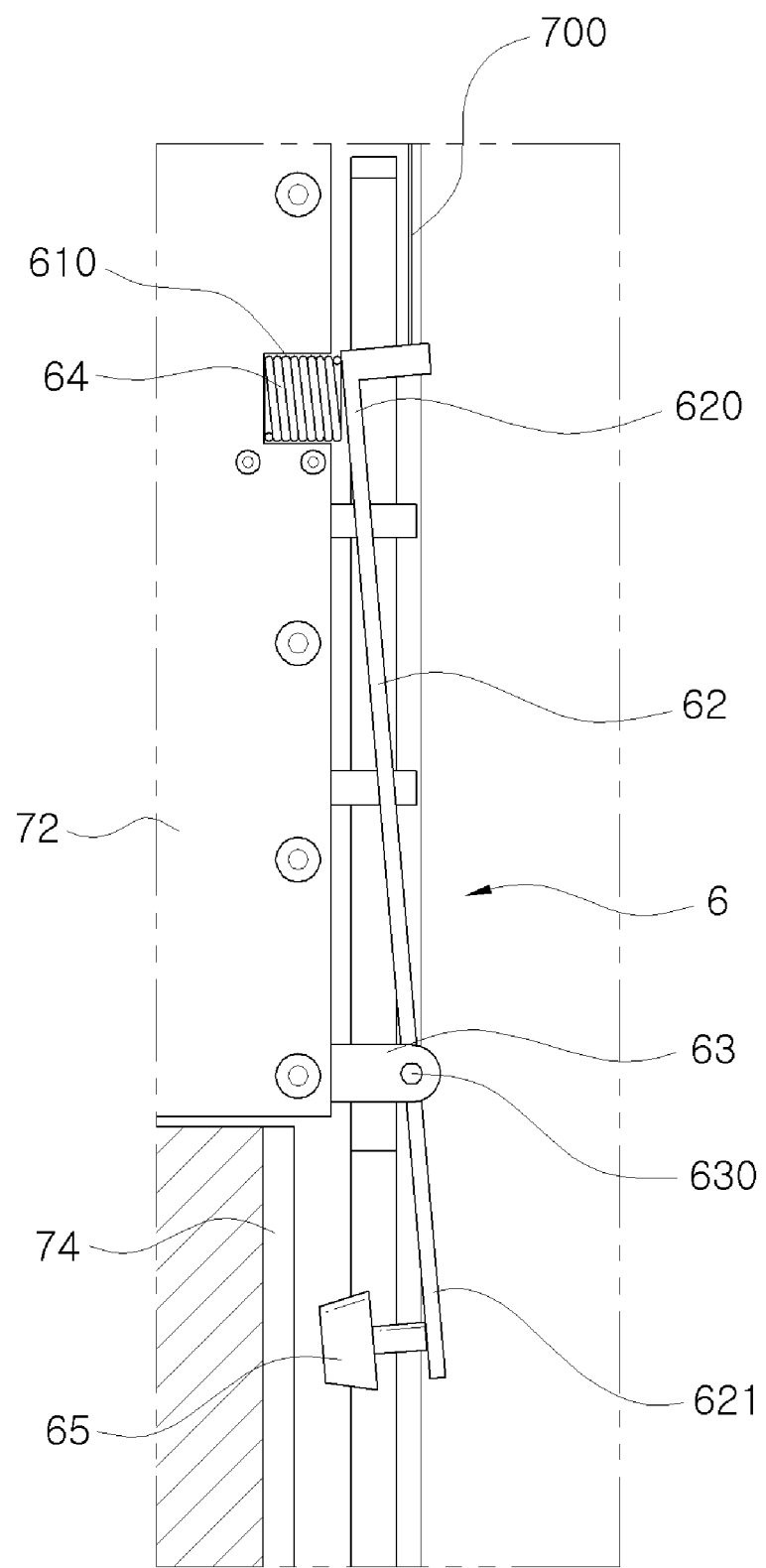
FIGS. 11 and 12 are views of the brake system according to an exemplary embodiment.
Figure 12:
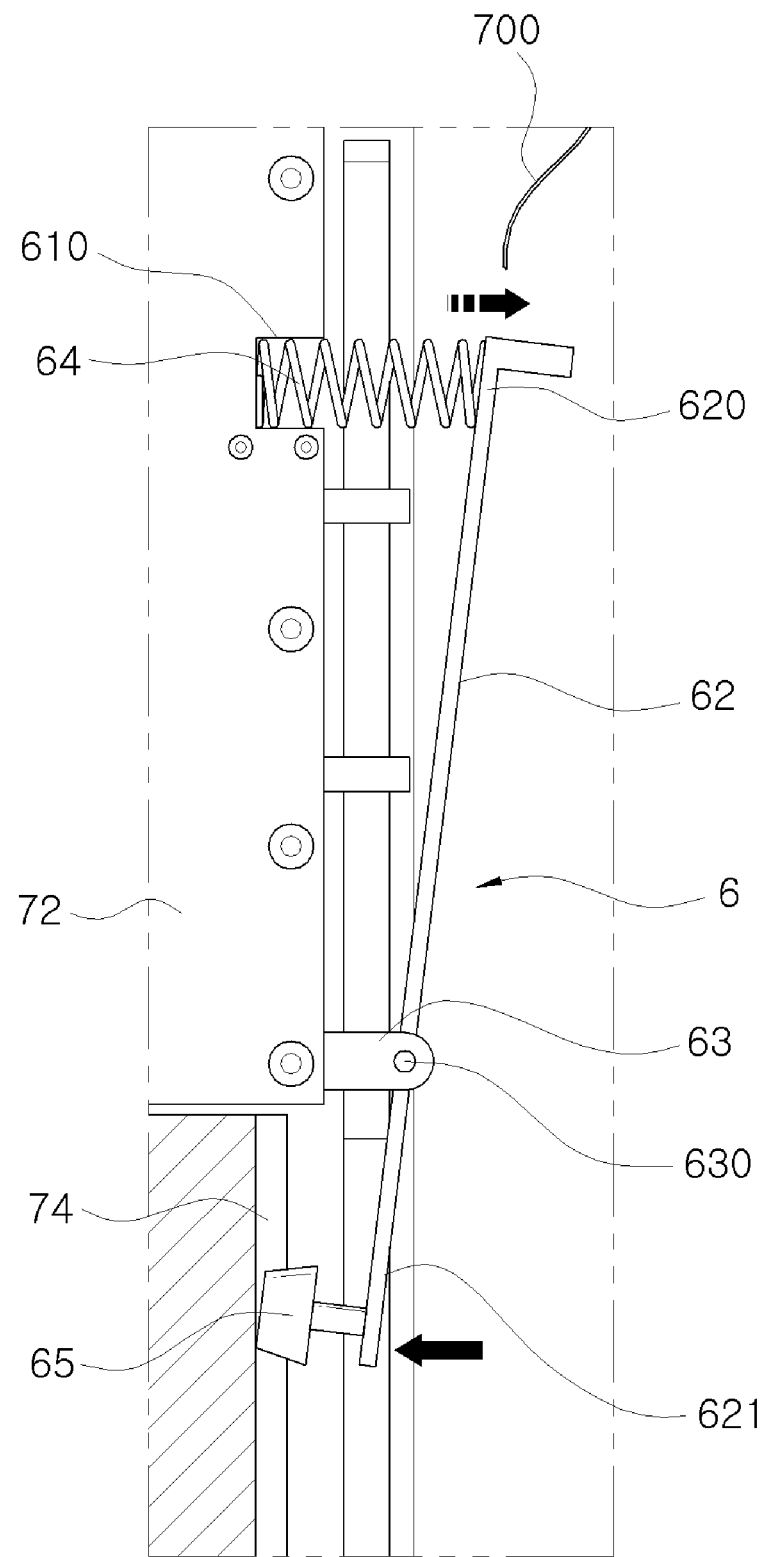

FIG. 10 is a view of a mammographic apparatus 7 including the brake system 6 according to an exemplary embodiment. FIGS. 11 and 12 are views of the brake system 6 according to an exemplary embodiment.

Referring to FIGS. 10 to 12, the brake system 6 may be provided to prevent a body (not shown) of the mammographic apparatus 7 from falling. The body of the mammographic apparatus 7 may be provided to be movable up and down along a stand 70.

The body may move along an elevating shaft 73 disposed on the stand 70 and extending upward and downward. The body may be connected to the elevating shaft 73 via a mobile panel 72. The mobile panel 72 is mounted on the elevating shaft 73 and moves up and down along the elevating shaft 73, thereby allowing the body to move up and down along the elevating shaft 73.

The mobile panel 72 may be connected to a cable 700 operated by a driving source 75 and may move up and down as the cable 700 rotates clockwise or counterclockwise, respectively. Pulleys 701 which respectively receive a driving force from the driving source 75 may be provided on a top and a bottom of the stand 70. The cable 700 may be wound on the pulleys 701 and may rotate together with the pulleys 701. The mobile panel 72 may include the brake system 6. The stand 70 may include a rail unit 74 extending upward and downward. The rail unit 74, similar to the rail unit 50, may include a bottom part and side parts extending from the bottom part. The side parts may be provided on both sides of the bottom part to face each other. Inner surfaces of the side parts may be provided to be tapered. That is, a greater distance between the inner surfaces of the side parts may be formed farther from the bottom part.

The brake system 6 may include a lever unit 62 and an elastic member 64. The lever unit 62 may be mounted on the mobile panel 72 by a mounting bracket 63. Here, the lever unit 62 may be disposed to extend upward and downward to be parallel to the elevating shaft 73. The lever unit 62 may be rotatably provided on a rotational shaft 630 which passes through the mounting bracket 63 and the lever unit 62. The lever unit 62 rotates with respect to the rotational shaft 630.

The cable 700 may be mounted on one side of the lever unit 62. A wedge 65 which is insertable into the rail unit 74 may be provided on the other side opposite to the one side of the lever unit 62. The wedge 65 may be formed to allow an outer surface thereof to correspond to a tapered shape of an inner surface of the rail unit 74. When an upper part of the lever unit 62 based on the rotational shaft 630 is designated as a first lever part 620 and a lower part of the lever unit 62 is designated as a second lever part 621, the cable 700 may be mounted on an end of the first lever part 620 and the wedge 65 may be located on an end of the second lever part 621. The end of the first lever part 620 is tilted to be positioned close to the mobile panel 72 due to the cable 700 mounted on the end of the first lever part 620, and the end of the second lever part 621 may be provided to be positioned away from the mobile panel 72 as shown in FIG. 11. The wedge 65 located on the end of the second lever part 621 may be separate from the mobile panel 72 and the rail unit 74.

An elastic member container 610 may be provided on one side of the mobile panel 72. The elastic member container 610 may accommodate the elastic member 64. The elastic member container 610 may be located to allow the elastic member 64 accommodated in the elastic member container 610 to push away the first lever part 620 from the mobile panel 72.

When the mobile panel 72 normally ascends and descends due to the cable 700, the elastic member 64 may maintain a state of being pressurized by the first lever part 620 while being accommodated in the elastic member container 610.

When the cable 700 breaks while the mammographic apparatus 7 is being used as shown in FIG. 12, the mobile panel 72 on which the body is mounted may descend due to the weights of the body and the mobile panel. Here, when the cable 700 breaks, a state in which the elastic member 64 is pressurized by the first lever part 620 may be released. The elastic member 64 may supply the elastic force to pressurize the first lever part 620 to become separate from the mobile panel 72. The lever unit 62 rotates with respect to the rotational shaft 630 in such a way that the wedge 65 provided on the end of the second lever part 621 may be inserted into the rail unit 74. Due to a descent of the body and the mobile panel 72, the wedge 65 may slide along the rail unit 74. The wedge 65 may slide on the rail unit 74 for a certain distance and then may be fixed by a frictional force between the wedge 65 and the rail unit 74 and a force of the wedge 65 to pressurize the inner surface of the rail unit 74, thereby halting the descent of the mobile panel 72 on which the body is mounted. Hereby, even when the cable 700 breaks, it is possible to prevent an accident such as a rapid descent of the body.

Figure 13:
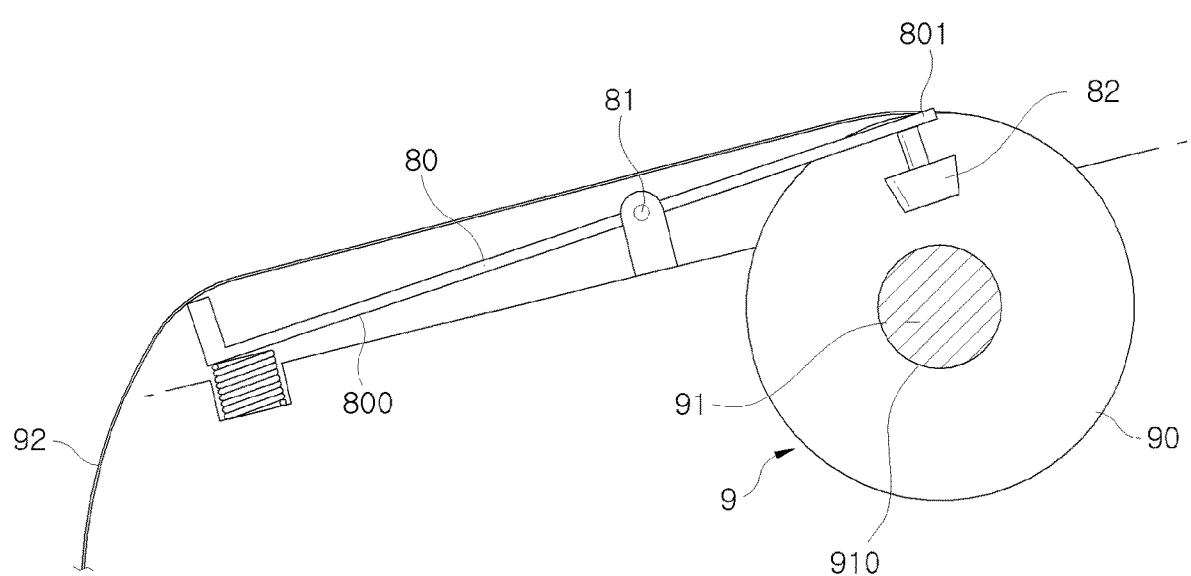
FIGS. 13 and 14 are views of a brake system according to still an exemplary embodiment.
Figure 14:
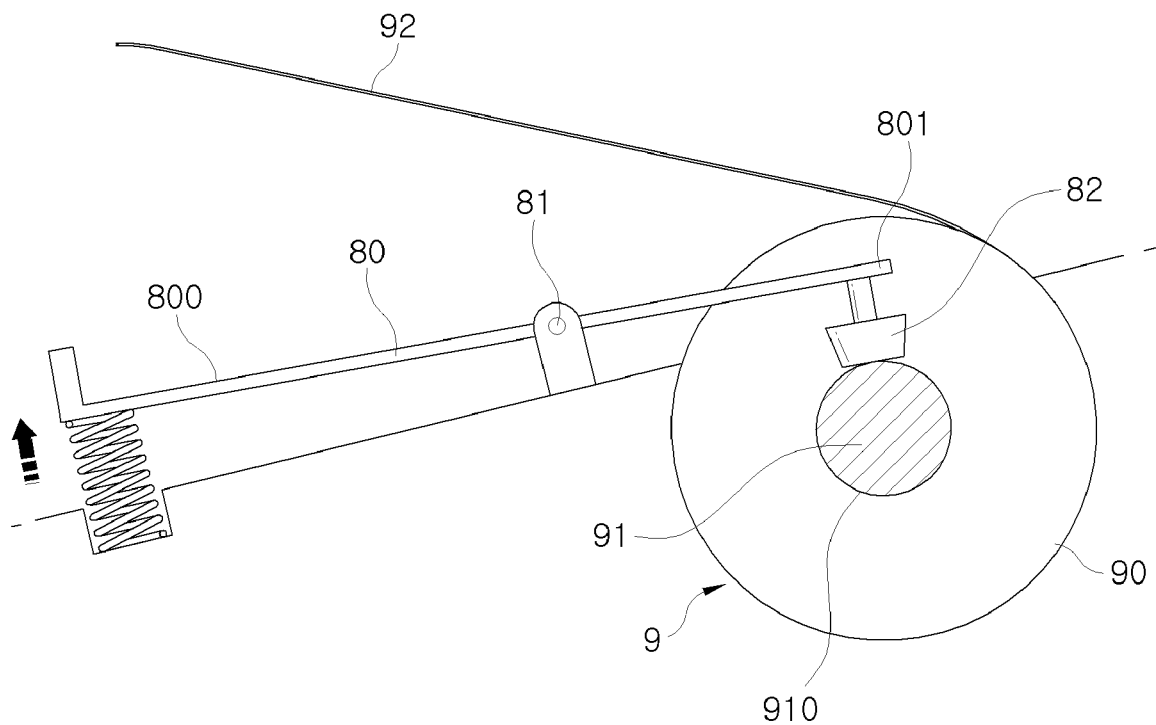

FIGS. 13 and 14 are views of a brake system 8 according to an exemplary embodiment.

Referring to FIGS. 13 and 14, the brake system 8 may be provided to halt a rotation of a brake shaft 91. As an example, the brake system 8 may be provided in a driving device 9 which increases or decreases a length of a column on which an X-ray generator is mounted. When a cable 92 provided in the driving device 9 breaks, driving of the driving device 9 may be halted by the brake system 8. A device on which the brake system 8 is mounted is not limited thereto.

Hereinafter, a case in which the driving device 9 includes a rotational body 90 and the brake shaft 91 mounted on the rotational body 90 and the rotational body 90 receives a driving force through the cable 92 will be described. The brake system 8 may operate and halt a rotation of the rotational body 90 when the cable 92 breaks.

The brake system 8 may include a lever unit 80 and an elastic member 83. The lever unit 80 may be rotatably provided on a lever-rotational shaft 81. That is, the lever unit 80 rotates with respect to the lever-rotational shaft 81. Based on the lever-rotational shaft 81, one side of the lever unit 80 is designated as a first lever part 800 and the other side thereof is designated as a second lever part 801. The lever-rotational shaft 81 may be located closer to an end of the second lever part 801 than an end of the first lever part 800 as shown in FIG. 13.

The elastic member 83 may be located on a side of the first lever part 800. The elastic member 83 may be provided to apply pressure to the first lever part 800 when there is no external force. When the driving device 9 normally operates, one side of the first lever part 800 may be pushed by the cable 92. Here, the elastic member 83 may be compressed by the first lever part 800.

Hereinafter, a case in which the first lever part 800 receives a force which allows the first lever part 800 to face downward by the cable 92 located above the first lever part 800 and the elastic member 83 is located below the first lever part 800 will be described. Positions and force transfer directions of the cable 92, the first lever part 800, and the elastic member 83 are not limited thereto.

A wedge 82 may be provided on a side of the second lever part 801. The wedge 82 may be provided to be in contact with an outer surface 910 of the brake shaft 91 according to rotation of the lever unit 80. At least one of the outer surface 910 of the brake shaft 91 and an outer surface of the lever unit 80 may be surrounded with a material having a high friction coefficient.

When the cable 92 does not break and the driving device 9 normally operates, the wedge 82 is separated from the outer surface 910 of the brake shaft 91. Here, the brake shaft 91 and the rotational body 90 may rotate clockwise or counterclockwise.

When the cable 92 breaks, the force which is applied to the first lever part 800 may be removed. When the force which is applied to the first lever part 800 is removed, the first lever part 800 may rotate on the lever-rotational shaft 81 due to an elastic force of the elastic member 83 to allow the end of the first lever part 800 to face upward. Here, the second lever part 801 may move toward the brake shaft 91 and may be in contact with the outer surface 910 of the brake shaft 91.

A rotation speed of the brake shaft 91 may be gradually slow down and the brake shaft 91 may stop the rotation due to a frictional force with the outer surface of the wedge 82. The brake shaft 91 stops the rotation, thereby allowing the rotational body 90, on which the brake shaft 91 is mounted, to stop a rotation thereof.

As described above, even when the cable 92 of the driving device 9 breaks, the rotation of the rotational body 90 is halted by the brake system 8, thereby preventing the column on which the X-ray generator is mounted from rapidly descending.

As is apparent from the above description, a tomograph in accordance with one embodiment of the present invention obtains definite images of an object by preventing a body from moving by using a brake system.

While exemplary embodiments have been particularly shown and described above, it would be appreciated by those skilled in the art that various changes may be made therein without departing from the principles and spirit of the inventive concept, which is defined in the following claims.

What is claimed is:

1. An X-ray imaging apparatus comprising:
a stand;
a body provided to be movable along the stand;
a cable provided to allow the stand to be movable; and
a brake apparatus provided to halt a movement of the body,
wherein the brake apparatus comprises:
a lever unit configured to rotate with respect to a rotational shaft and including a first end and a second end opposite to the first end; and
a wedge provided on the second end of the lever unit, and
wherein the wedge is provided to halt the movement of the body when the cable breaks.

2. The X-ray imaging apparatus of claim 1, wherein the stand includes a rail unit, and
wherein the wedge is inserted into the rail unit when the cable breaks and the movement of the body is halted by a frictional force generated between the wedge and the rail unit.

3. The X-ray imaging apparatus of claim 2, wherein the brake apparatus further comprises an elastic member provided on the first end of the lever unit and configured to provide an elastic force to rotate the lever unit.

4. The X-ray imaging apparatus of claim 3, wherein when the cable breaks, a state in which the elastic member is pressurized by the first end of the lever unit is released, and the lever unit rotates so that the wedge is inserted into the rail unit.

5. The X-ray imaging apparatus of claim 2, wherein the body moves upward and downward along the stand, and
wherein the rail unit is formed on the stand to extend along a movement direction of the body.

6. The X-ray imaging apparatus of claim 1, further comprising:
pulleys rotatably provided to wind the cable; and
a driving source provided to rotate the pulleys.

7. The X-ray imaging apparatus of claim 3, further comprising a mobile panel provided to couple the body and the stand,
wherein the body is movably coupled to the stand via the mobile panel, and
wherein the mobile panel is provided with an elastic member container to accommodate the elastic member.

8. An X-ray imaging apparatus comprising:
a column on which an X-ray generator is mounted;
a driving device rotatably provided to increase or decrease a length of the column;
a cable coupled to the driving device to drive the driving device; and
a brake apparatus provided to halt driving of the driving device,
wherein the brake apparatus comprises:
a lever unit configured to rotate with respect to a rotational shaft and including a first end and a second end opposite to the first end; and
a wedge provided on the second end of the lever unit, and
wherein the wedge is provided to halt a rotation of the driving device by contacting to the driving device when the cable breaks.

9. The X-ray imaging apparatus of claim 8, wherein the driving device comprises:
a brake shaft; and
a rotational body configured to rotate with respect to the brake shaft, and
wherein the wedge is provided to halt a rotation of the rotational body by contacting to the brake shaft when the cable breaks.

10. The X-ray imaging apparatus of claim 9, wherein at least one of an outer surface of the brake shaft and an outer surface of the wedge is surrounded with a material having a high friction coefficient.

11. The X-ray imaging apparatus of claim 9, wherein the brake apparatus further comprises an elastic member provided on the first end of the lever unit and configured to provide an elastic force to rotate the lever unit.

12. The X-ray imaging apparatus of claim 11, wherein when the cable breaks, a state in which the elastic member is pressurized by the first end of the lever unit is released, and the lever unit rotates so that the wedge is contacted to the brake shaft.

* * * * *